(12) United States Patent
Schreiber et al.

(10) Patent No.: US 7,485,653 B2
(45) Date of Patent: Feb. 3, 2009

(54) 1,4-DIHYDROPYRIDINE COMPOUNDS, PHARMACEUTICAL COMPOSITIONS, AND METHODS FOR THE TREATMENT OF CARDIOVASCULAR DISEASE

(75) Inventors: Kathy Schreiber, Westminister, CO (US); Larry Melvin, Longmont, CO (US)

(73) Assignee: Gilead Sciences, Inc., Foster City, CA (US)

(*) Notice: Subject to any disclaimer, the term of this patent is extended or adjusted under 35 U.S.C. 154(b) by 529 days.

(21) Appl. No.: 10/980,605

(22) Filed: Nov. 3, 2004

(65) Prior Publication Data

US 2005/0124633 A1 Jun. 9, 2005

Related U.S. Application Data

(60) Provisional application No. 60/516,828, filed on Nov. 3, 2003.

(51) Int. Cl.
  C07D 211/02 (2006.01)
  C07D 401/02 (2006.01)
  A61K 31/44 (2006.01)
(52) U.S. Cl. .................. 514/344; 514/336; 514/340; 514/341; 546/268.1; 546/268.4; 546/286
(58) Field of Classification Search .................. None
  See application file for complete search history.

(56) References Cited

U.S. PATENT DOCUMENTS 5,604,251 A 2/1997 Heitsch et al. .............. 514/396

FOREIGN PATENT DOCUMENTS

| EP | 0273349 | 7/1988 |
|---|---|---|
| WO | WO 98/33791 | 5/1994 |
| WO | WO 03/062201 | 7/2003 |
| WO | WO 03/088970 | 10/2003 |

OTHER PUBLICATIONS

Eichhorn and Bristow, "Medical Therapy Can Improve the Biological Propreties of the Chonically Failing Heart: A New Era in the Treatment of Heart Failure," *Circulation*, 94:2285-2296, 1996.
Hajjar et al., "Cross-Bridge Dynamics in Human Ventricular Myocardium: Regulation of Contractility in the Failing Heart," *Circulation*, 86(6):1819-1826, 1992.
Krauze and Duburs, "Synthesis and Properties of 3-Cyano-4-(4-Cyanophenyl)-1,4-Dihydropyridine-2(3H)-Thiones," *Chemistry of Heterocyclic Compounds*, 36:693-697, 2000.
Krauze et al., "Efficient Regioselective One-pot Synthesis of Partially Hydrogenated Thiazolo [3,2-a]pyridines," *Tetrahedron*, 54:9161-9168, 1998.
Krauze et al., "Synthesis and cardiovascular activity of 4-substituted 2-alkythio-1,4-dihydropyridines," *Khimiko-Farmatsevticheskii Zhurnal*, 22: 955-959, 1988.

Krauze et al., "СЗНТЕЗ ЗЗММУНОТРОПНАЯ АКТЗ ВНОСУЬПРОЙЗВОДНЬ IX ТЗА30ПО [3,2]-БЕН3 3М3ДИЬА3О БА," *Khimiko-Farmatsevticheskii Zhurnal*, 25;40-42, 1991 (English Abstract).
Krauze et al., "СЗНТЕЗ, СВОЙСТВА 3КАРПЗОВАСКУПЯ РНАЯАКТЗВНОСТЬ 3АМЕЩЕННЫХ 4-ДИЬЗДИЬ3 РО3ДИЬР3ДИЬ3Н-2{3Н}-Т3ОНОВ," *Khimiko-Farmatsevticheskii Zhurnal*, 22:548-553, 1988 (English Abstract).
Lowes et al., "Changes in gene expression in the intact human heart. Downregulation of alpha-myosin heavy chain in hypertrophied, failing ventricular myocardium," *J. Clin. Invest.*, 100(9):2315-2324, 1997.
Lowes et al., "Myocardial gene expression in dilated cardiomyopathy treated with beta-blocking agents," *N. Engl. J. Med.*, 346(18):1357-1365, 2002.
Marian and Roberts, "Recent Advances in the Molecular Genetics of Hypertrophic Cardiomyopathy," *Circulation*, 92:1336-1347, 1995.
Miyata et al., "Myosin heavy chain isoform expression in the failing and nonfailing human heart," *Circ. Res.*, 86(4):386-390, 2000.
Nakao et al., "Myosin heavy chain gene expression in human heart failure," *J. Clin. Invest.*, 100(9):2362-2370, 1997.
Niimura et al., "Sarcomere Protein Gene Mutations in Hypertrophic Cardiomyopathy of the Elderly," *Circulation*, 105(4):446-451, 2002.
Pagani et al., "Changes in myofibrillar content and Mg-ATPase activity in ventricular tissues from patients with heart failure caused by coronary artery disease, cardiomyopathy, or mitral valve insufficiency," *Circ. Res.*, 63(2):380-385, 1988.
Raizada et al., "Age-related difference in cardiac adaptation to chronic hypertension in rats, with and without nifedipine treatment," *Molecular and Cell Biochemistry*, 198: 109-112, 1999.
Raizada et al., "Alterations in cardiac myosin isozymes associated with aging and chronic hyperextension: their modulation with nifedipine," *Cardiovascular Res.*, 27:1869-1872, 1993.
Reiser et al., "Human cardiac myosin heavy chain isoforms in fetal and failing adult atria and ventricles," *Am. J. Physiol. Heart. Circ. Physiol.*, 280(4):H1814-H1820, 2001.
Samarel et al., "Contractile arrest accelerates myosin heavy chain degradation in neonatal rat heart cells," *American J. Physiology*, 263:C642-C652, 1992.
Schwartz et al., "Molecular Basis of Familial Cardiomyopathies," *Circulation*, 91:532-540, 1995.
Sharanin et al., "РЕАКЦИИИЛИДИЛИДИЛИД АРИЛИДИДЬИЛИДЦИЕНЦИИИЛИДАНОТИЛИДОА ЦИИ ЕТАМИЛИДЦИОВ С КАРИОНИЛИДИДЬ ЦМИЛИДСОЕ ЦИИ ИЛИДНЕНИЛИДИДМИЛИДИЛИДХ ЕНАМИНАМИЛИД," *Zhurnal Organicheskoi Khimii*, 21:683-684, 1985.
Sharanin et al., "РЕАКЦИИИЛИДИЛИДЦИИИЛИДК ИДЬ ИЛИДЗАЦИИИЛИД,ИЛИД НИЛИДТРИЛИДИДЬОВ," *Zhurnal Organicheskoi Khimii*, 22:2600-2609, 1986.
Simpson et al., "Mechanical regulation of cardiac myocyte protein turnover and myofibrillar structure," *American J. Physiology*, 270:C1075-C1087, 1996.

(Continued)

*Primary Examiner*—Zinna N Davis
(74) *Attorney, Agent, or Firm*—Fulbright & Jaworski, LLP

(57) ABSTRACT

The present invention provides certain substituted 1,4-dihydropyridine compounds, including pure enantiomeric forms and pharmaceutical formulations thereof. These compounds provide for elevation of α-MyHC protein levels and α-MyHC mRNA levels, and most frequently these same compounds provide simultaneous lowering of β-MyHC protein levels and β-MyHC mRNA levels. Thus, these compounds may be used alone or in conjunction with other drugs to treat heart failure.

13 Claims, 2 Drawing Sheets

OTHER PUBLICATIONS

Thierfelder et al., "Alpha-tropomyosin and cardiac troponin T mutations cause familial hypertrophic cardiomyopathy: a disease of the sarcomere," *Cell*, 77:701-712, 1994.

Tirzite et al., "Synthesis and Antiradical Activity of 5-Acetyl-2Alkythio-4-Aryl-6-Methyl-1,4-Dihydropyridine-3-caboxcylic acid nitrile," *Chem. Heterocyclic Compounds*, 38:795-800, 2002.

Watkins et al., "Characteristics and prognostic implications of myosin missense mutations in familial hypertrophic cardiomyopathy," *N. Engl. J. Med.*, 326:1108-1114, 1992.

Yamazaki et al., "Efficient Inhibition of the Development of Cardiac Remodeling by a Long-Acting Calcium Antagonist Amlodipine," *Hypertension*, 31:32, 1998.

Abraham et al., "Coordinate changes in Myosin heavy chain isoform gene expression are selectively associated with alterations in dilated cardiomyopathy phenotype," *Mol Med.*, 8(11):750-760, 2002.

Bouvagnet et al., "Distribution pattern of alpha and beta myosin in normal and diseased human ventricular myocardium," *Basic Res. Cardiol.*, 84:91-102, 1989.

Bristow, "Beta-Andrenergic Receptor Blockade in Chronic Heary Failure," *Circulation*, 101(5):558-569, 2000.

Bristow, "Mechanisms of Development of Heat Failure in Hypertensive Patient," *Cardiology*, 92:3-6, 1999.

Database Chemcats Order Nos. 3012-0085, 0077, 2636-0074, 0073, 0067, 0066, 0064, 0060, 0061, 0057, 0048, 0046, 0041, 0034, 8009-1283 abstract, Apr. 2003.

Dipla et al., "Myocyte recovery after mechanical ciculatory support in humans with end-stage heart failure," *Circulation*, 97(23):2316-2322, 1998.

1,4-DIHYDROPYRIDINE COMPOUNDS, PHARMACEUTICAL COMPOSITIONS, AND METHODS FOR THE TREATMENT OF CARDIOVASCULAR DISEASE

This application claims benefit of priority to U.S. Provisional Application Ser. No. 60/516,828, filed Nov. 3, 2003, the entire contents of which are hereby incorporated by reference.

BACKGROUND OF THE INVENTION

A. Field of the Invention

This invention relates to compounds, pharmaceutical compositions and methods for the treatment of myosin heavy chain (MyHC)-mediated diseases, and in particular, heart failure.

B. Related Art

Heart failure is a pathophysiological state in which the heart fails to pump blood at a rate commensurate with the requirements of the metabolizing tissues of the body. It is caused in most cases—about 95% of the time—by myocardial failure.

The contractile proteins of the heart lie within the muscle cells, called myocytes, which constitute about 75% of the total volume of the myocardium. The two major contractile proteins are the thin actin filament and the thick myosin filament. Each myosin filament contains two heavy chains and four light chains. The bodies of the heavy chains are intertwined, and each heavy chain ends in a head. Each lobe of the bi-lobed myosin head has an ATP-binding pocket, which has in close proximity the myosin ATPase activity that breaks down ATP to its products.

The velocity of cardiac muscle contraction is controlled by the degree of ATPase activity in the head regions of the myosin molecules. The major determinant of myosin ATPase activity and, therefore, of the speed of muscle contraction, is the relative amount of the two myosin heavy chain isomers, α and β (MyHC). The α-MyHC isoform has approximately 2-3 times more enzymatic activity than the β-MyHC isoform and, consequently, the velocity of cardiac muscle shortening is related to the relative percentages of each isoform. For example, adult rodent ventricular myocardium has approximately 80-90% α-MyHC, and only 10-20% β-MyHC, which explains why its myosin ATPase activity is 3-4 times greater than bovine ventricular myocardium, which contains 80-90% β-MyHC.

When ventricular myocardial hypertrophy or heart failure is created in rodent models, a change occurs in the expression of MyHC isoforms, with α-MyHC decreasing and β-MyHC increasing. These "isoform switches" reduce the contractility of the hypertrophied rodent ventricle, ultimately leading to myocardial failure. This pattern of altered MyHC gene expression has been referred to as reversion to a "fetal" expression pattern because, during fetal and early neonatal development, β-MyHC also dominates in rodent ventricular myocardium.

It has been shown that myocardial function declines with age in animals. Cellular and molecular mechanisms that account for age-associated changes in myocardial performance have been studied largely in rodents. Among other changes, marked shifts in MyHC occur in rodents, i.e., the β isoform becomes predominant in senescent rats. Steady-state mRNA levels for α-MyHC and β-MyHC parallel the age-associated change in the MyHC proteins. The myosin ATPase activity declines with the decline in α-MyHC content, and the altered cellular profile results in a contraction that exhibits a reduced velocity and a prolonged time course.

Human atrial myocardium may undergo similar isoform switches with hypertrophy or failure, although human ventricular myocardium, the basis for the majority of cases of heart failure (greater than 90% of cases), has not been consistently shown to exhibit this pattern. Several studies have examined this issue in autopsy cases, but did not find biologically significant expression of the α-MyHC isoform in putatively normal hearts. Since there was thought to be no significant expression of α-MyHC in normal hearts, a down-regulation in α-MyHC was not thought to be a possible basis for myocardial failure in humans. There was one early report that the amount of α-MyHC, although extremely small to begin with, was reduced in failing human myocardium. (Bouvagnet, 1989). However, more recent reports have shown the existence of appreciable levels of a-MyHC in the human heart at both the mRNA and protein level. At the mRNA level, 23-34% of the total ventricular mRNA is derived from α-MyHC (Lowes et al., 1997; Nakao et al., 1997), while approximately 1-10% of the total myosin protein content is α-MyHC (Miyata et al., 2000; Reiser et al., 2001). These changes in MyHC isoform content are sufficent to explain the decrease in myosin or myofibrillar ATPase activity in the failing human heart (Hajjar et al., 1992; Pagani et al., 1988).

Data generated in the 1990's suggested that β myosin heavy chain mutations may account for approximately 30-40% percent of cases of familial hypertrophic cardiomyopathy (Watkins et al., 1992; Schwartz et al., 1995; Marian and Roberts, 1995; Thierfelder et al., 1994; Watkins et al., 1995). A patient with no family history of hypertrophic cardiomyopathy presented with late-onset cardiac hypertrophy of unkonwn etiology, and was shown to have a mutation in α-MyHC (Niimura et al., 2002). Two important studies have shown even more convincingly the important role of the MyHC isoforms in cardiovascular disease. Lowes et al. (2002) showed that using beta blockers to treat dilated cardiomyopathy led to increased levels of α-MyHC and decreased levels of β-MyHC that directly corresponded to improvement in disease state. In fact, the changes in α-MyHC noted in those studies was the only factor shown to correlate with improvement in cardiac function. Equally convincingly, Abraham et al. (2002) have shown that myosin heavy chain isoform changes directly contribute to disease progression in dilated cardiomyopathy. These studies show the importance and need for an agent that can alter, if not reverse, the isoform switching that occurs in the MyHC isoforms in cardiovascular disease.

SUMMARY OF THE INVENTION

Accordingly the present invention provides for the novel chiral and optically active compounds of Formula I, and pharmaceutically acceptable salts thereof.

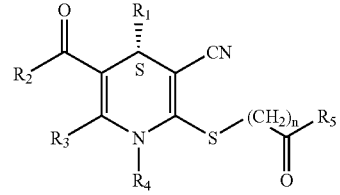

Formula I $R_1$ and $R_5$ are, independently, phenyl, pyridine, pyrimidine, thiophene, furan, oxazole, isoxazole, thiazole, isothiazole, imidazole and pyrazole, and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2NH$—$C_{0-4}$-alkyl, $SO_2N(C_{1-4}$-alkyl$)_2$, $NHSO_2$—$C_{1-4}$-alkyl, CONH—$C_{0-4}$- alkyl, NHCO—$C_{1-4}$-alkyl and COO—$C_{0-4}$-alkyl; $R_2$ is $C_{1-4}$-alkyl, $R_3$ and $R_4$ are $C_{0-4}$-alkyl; and alkyl may be straight or branched chain; and n is 1-4; and further comprising all diastereomers.

One class of compounds within the embodiment of this invention are compounds of Formula I wherein $R_1$ and $R_5$ are, independently, phenyl, thiophene, furan, oxazole and thiazole; and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2NH$—$C_{0-4}$-alkyl, $SO_2N(C_{1-4}$-alkyl$)_2$, $NHSO_2$—$C_{1-4}$-alkyl, CONH—$CO_{0-4}$-alkyl, NHCO—$C_{1-4}$— alkyl and COO—$C_{0-4}$-alkyl. A preferred class of compounds are compounds of Formula I wherein $R_1$ and $R_5$ are, independently, phenyl, thiophene and furan; and any of $R_1$ and $R_5$ may be optionally substituted by one or more of halogen, $NO_2$, CN, $CF_3$, $C_{1-4}$-alkyl, $C_{0-4}$-alkyl-O, $(C_{1-4}$-alkyl$)_2$—N, $SO_2NH$—$C_{0-4}$-alkyl, $NHSO_2$—$C_{1-4}$-alkyl, CONH—$C_{0-4}$-alkyl, NHCO—$C_{1-4}$-alkyl and COO—$C_{0-4}$-alkyl; and $R_3$ is $C_{1-4}$-alkyl.

A more preferred class of compounds are compounds of Formula I wherein $R_1$ and $R_5$ are, independently, phenyl, thiophene and furan; and any of $R_1$ and $R_5$ may be optionally substituted by one or more of halogen, $NO_2$, CN, $CF_3$, $C_{1-4}$-alkyl, $CO_4$-alkyl-O, $(C_{1-4}$-alkyl$)_2$—N, $SO_2NH$—$C_{0-4}$-alkyl, $NHSO_2$—$C_{1-4}$-alkyl, CONH—$C_{0-4}$-alkyl, NHCO—$C_{1-4}$-alkyl and COO—$C_{0-4}$-alkyl, $R_2$ and $R_3$ are $CH_3$, $R_4$ is $C_{0-1}$-alkyl, and n is 1-2. An even more preferred class of compounds are compounds of Formula I wherein $R_1$ and $R_5$ are phenyl and any of $R_1$ and $R_5$ may be optimally substituted by one or more of Br, Cl, F, $NO_2$, $CF_3$, $CH_3$, $CH_3O$, $(C_{1-4}$-alkyl$)_2$— N, CONH—$C_{0-4}$-alkyl, NHCO—$C_{1-4}$-alkyl and COO—$C_{0-4}$-alkyl, $R_2$ and $R_3$ are $CH_3$, $R_4$ is H and n is 1-2.

Especially preferred are compounds of Formula I wherein $R_1$ and $R_5$ are phenyl and any of $R_1$ and $R_5$ may be optimally substituted by one or more of Br, Cl, F, $NO_2$, $CF_3$, $CH_3$, $CH_3O$, $(C_{1-4}$-alkyl$)_2$—N, CONH—$C_{0-4}$-alkyl, NHCO—$C_{1-4}$- alkyl and COO—$C_{0-4}$-alkyl, $R_2$ and $R_3$ are $CH_3$, $R_4$ is H and n is 1. The most preferred compounds of Formula I are compounds wherein $R_1$ and $R_5$ are phenyl and any of $R_1$ and $R_5$ may be optimally substituted by one or more of Cl, F, $NO_2$, $CF_3$, $CH_3$, $CH_3O$, $R_2$ and $R_3$ are $CH_3$, $R_4$ is H and n is 1.

In a further embodiment of the invention, the formulation comprises the compounds of Formula I with this S enantiomer being substantially purified from the R enantiomer. Contemplated forms of the invention have the S form being greater than 75% pure, greater than 80% pure, greater than 85% pure, greater than 90% pure, greater than 95% pure, greater than 96% pure, greater than 97% pure, greater than 98% pure, and greater than 99% pure.

In a one further embodiment of the invention, the formulation comprises the compounds of Formula II:

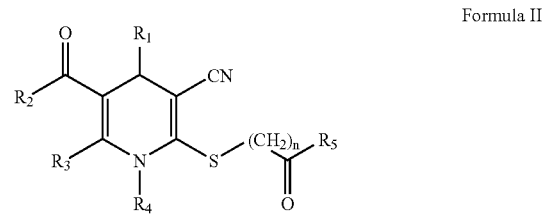

Formula II and pharmaceutically acceptable salts thereof, wherein:

$R_1$ and $R_5$ are, independently, phenyl, pyridine, pyrimidine, thiophene, furan, oxazole, isoxazole, thiazole, isothiazole, imidazole and pyrazole; and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2NH$—$C_{0-4}$-alkyl, $SO_2N(C_{1-4}$-alkyl$)_2$, $NHSO_2$—$C_{1-4}$-alkyl, CONH—$C_{0-4}$-alkyl, NHCO—$C_{1-4}$-alkyl and COO—$C_{0-4}$-alkyl; $R_2$ is $C_{1-4}$-alkyl, $R_3$ and $R_4$ are $C_{0-4}$-alkyl, and alkyl may be straight or branched chain; and n is 1-4; and further comprising all diastereomers.

In specific embodiments of the invention, the compounds and pharmaceutical formulations listed above are administered in an amount and through a route sufficient to achieve an upregulation of the α-myosin heavy chain (α-MyHC) mRNA levels in cardiomyocytes. Also contemplated is upregulating the protein levels of α-MyHC. In a further aspect of the invention, the formulation is administered in an amount and route sufficient to achieve an increase in the contractility of cardiomyoctes. In a further embodiment, there is disclosed a method of inducing a reversal of the remodeling that occurs in hypertrophic or failing heart tissue in vivo, comprising administering to a subject suffering from cardiac hypertrophy or heart failure an amount of the claimed formulation that is sufficient to induce reverse remodeling, remodeling being defined as a decrease in the expression of the fetal genes and an increase in the expression of normal cardiac genes.

It is contemplated that the formulations of the current invention will be administered to a cell, that cell being an intact cardiomyocyte. These cardiomyocytes are located in heart tissue and that heart may be the intact heart of a human patient. It is further contemplated that the formulations will be administered directly to the ventricle, and specifically the left ventricle of the heart. Routes include intra-aterial, intravenous, intramuscular and oral routes.

The formulations of the current invention may also be combined with, added to, or mixed with additional pharmaceutical formulations or treatment regimens given to the patient or to the heart or to the cardiomyocytes. These additional formulations may include, but are not limited to, "beta blockers," anti-hypertensives, cardiotonics, anti-thrombotics, vasodilators, hormone antagonists, endothelin antagonists, cytokine inhibitors and/or blockers, calcium channel blockers, phosphodiesterase inhibitors, and angiotensin type-2 antagonists. These drugs may be given before, at the same time as, or after the compounds of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
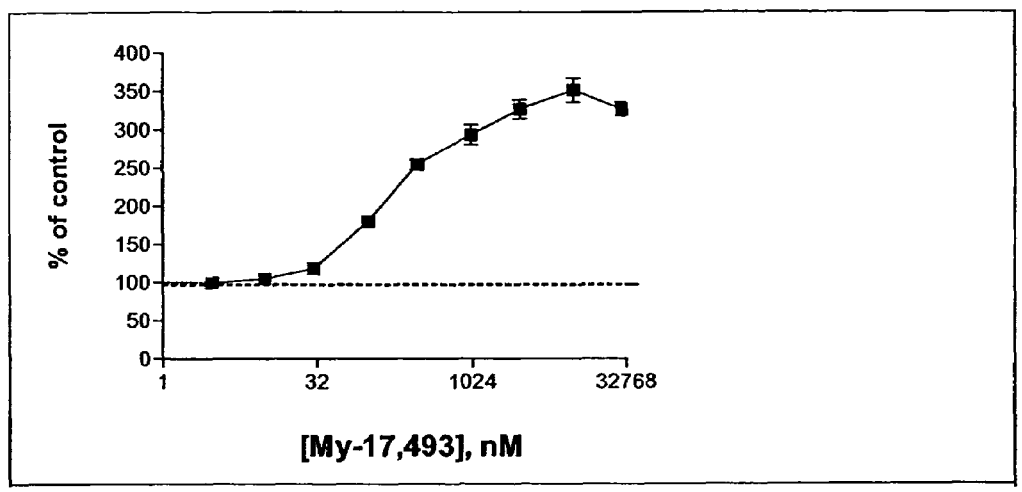
FIG. 1 Concentration-dependent effect of Compound 1 on αMyHC protein levels in the cytoblot assay. NRVM are cultured for 3 days in serum-free medium in the presence of differing amounts of Compound 1. At the end of the culture period, NRVM are fixed and analyzed for α-MyHC protein levels using the BA-G5 monoclonal antibody specific for α-MyHC. Results are collected as RLU using a Packard Fusion Plate reader, and normalized to the signal from samples cultured in the absence of compound (control, set to 100%).

The present invention provides for the novel optically active chiral compounds of Formula I:

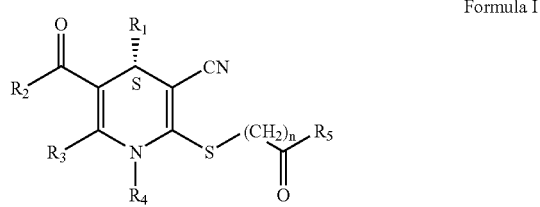

Formula I and pharmaceutically acceptable salts thereof, useful in the treatment of cardiovascular disease. The present inventors have unexpectedly found that the S enantiomer of certain substituted 1,4-dihydropyridine compounds (Formula I) provide surprising elevation of α-MyHC protein levels and α-MyHC mRNA levels and most frequently these same compounds provide simultaneous lowering of β-MyHC protein levels and β-MyHC mRNA levels. These embodiments are described in greater detail below.

I. Cardiovascular Diseases

Heart failure is one of the leading causes of morbidity and mortality in the world. In the U.S. alone, estimates indicate that 3 million people are currently living with cardiomyopathy, and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familial dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic form of DCM, as is disease associated with infectious sequelae. In sum, cardiomyopathies, including DCM, are significant public health problems.

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. Two particularly severe manifestations of heart disease are myocardial infarction and cardiac hypertrophy.

With respect to myocardial infarction, typically an acute thrombocytic coronary occlusion occurs in a coronary artery as a result of atherosclerosis and causes myocardial cell death. Because cardiomyocytes are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

With respect to cardiac hypertrophy, one theory regards this as a disease that resembles aberrant development and, as such, raises the question of whether developmental signals in the heart can contribute to hypertrophic disease. Cardiac hypertrophy is an adaptive response of the heart to virtually all forms of cardiac disease, including those arising from hypertension, mechanical load, myocardial infarction, cardiac arrhythmias, endocrine disorders, and genetic mutations in cardiac contractile protein genes. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

The causes and effects of cardiac hypertrophy have been extensively documented, but the underlying molecular mechanisms have not been fully elucidated. Understanding these mechanisms is a major concern in the prevention and treatment of cardiac disease and will be crucial as a therapeutic modality in designing new drugs that specifically target cardiac hypertrophy and cardiac heart failure. As pathologic cardiac hypertrophy typically does not produce any symptoms until the cardiac damage is severe enough to produce heart failure, the symptoms of cardiomyopathy are those associated with heart failure. These symptoms include shortness of breath, fatigue with exertion, the inability to lie flat without becoming short of breath (orthopnea), paroxysmal nocturnal dyspnea, enlarged cardiac dimensions, and/or swelling in the lower legs. Patients also often present with increased blood pressure, extra heart sounds, cardiac murmurs, pulmonary and systemic emboli, chest pain, pulmonary congestion, and palpitations. In addition, DCM causes decreased ejection fractions (i.e., a measure of both intrinsic systolic function and remodeling). The disease is further characterized by ventricular dilation and grossly impaired systolic function due to diminished myocardial contractility, which results in dilated heart failure in many patients. Affected hearts also undergo cell/chamber remodeling as a result of the myocyte/myocardial dysfunction, which contributes to the "DCM phenotype." As the disease progresses, so do the symptoms. Patients with DCM also have a greatly increased incidence of life-threatening arrhythmias, including ventricular tachycardia and ventricular fibrillation. In these patients, an episode of syncope (dizziness) is regarded as a harbinger of sudden death.

Diagnosis of dilated cardiomyopathy typically depends upon the demonstration of enlarged heart chambers, particularly enlarged ventricles. Enlargement is commonly observable on chest X-rays, but is more accurately assessed using echocardiograms. DCM is often difficult to distinguish from acute myocarditis, valvular heart disease, coronary artery disease, and hypertensive heart disease. Once the diagnosis of dilated cardiomyopathy is made, every effort is made to identify and treat potentially reversible causes and prevent further heart damage. For example, coronary artery disease and valvular heart disease must be ruled out. Anemia, abnormal tachycardias, nutritional deficiencies, alcoholism, thyroid disease and/or other problems need to be addressed and controlled.

As mentioned above, treatment with pharmacological agents still represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. The availability of new, safe and effective agents would undoubtedly benefit patients who either cannot use the pharmacological modalities presently available, or who do not receive adequate relief from those modalities. The prognosis for patients with DCM is variable, and depends upon the degree of ventricular dysfunction, with the majority of deaths occurring within five years of diagnosis. The inventors describe herein a novel therapeutic composition and methods for treating pathologic cardiac hypertrophy and heart failure.

II. 1,4-Dihydropyridine Compounds

As discussed above, the present invention provides for the novel, optically active chiral compounds of Formula I, pharmaceutically acceptable salts thereof, and their use in the treatment of cardiovascular disease. Compounds of formula I are members of the class of compounds known as substituted 1,4-dihydropyridine compounds. As a chemical class, 1,4-dihydropyridines are known to be useful for the treatment of hypertension and coronary artery spasm (angina) through a mechanism of action that involves binding to and blockade of L-type calcium channels in vascular smooth muscle. However, there have not been any previous reports that such compounds directly affect α-MyHC/β-MyHC expression levels.

Direct effects on the heart are usually not observed at clinically used doses of 1,4-dihydropyridine calcium channel blockers. These so-called calcium channel blocker drugs are reviewed in Goodman and Gilman's The Pharmacological Basis Of Therapeutics (2001). Drugs of this class that have been approved for marketing for use in humans are: amlodipine (The Merck Index, Number 491), aranidipine (The Merck Index, Number 772), bamidipine (The Merck Index, Number 1005), benidipine (The Merck Index, Number 1041), cilnidipine (The Merck Index, Number 2297), efonidipine (The Merck Index, Number 3555), felodipine (The Merck Index, Number 3981), isradipine (The Merck Index, Number 5262), lacidipine (The Merck Index, Number 5347), lercanidipine (The Merck Index, Number 5465), manidipine (The Merck Index, Number 5767), nicardipine (The Merck Index, Number 6520), nifedipine (The Merck Index, Number 6555), nilvadipine (The Merck Index, Number 6573), nimodipine (The Merck Index, Number 6579), nisoldipine (The Merck Index, Number 6593) and nitrendipine (The Merck Index, Number 6606). The chemical structures of these calcium channel blocker drugs are shown in the formulae below.

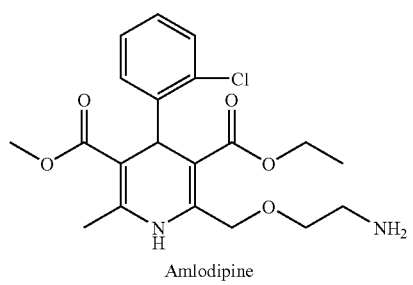
Amlodipine

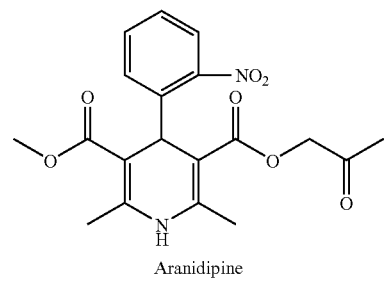
Aranidipine

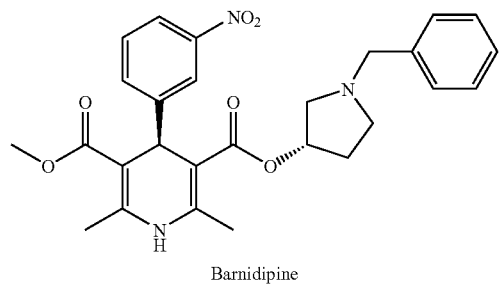
Barnidipine

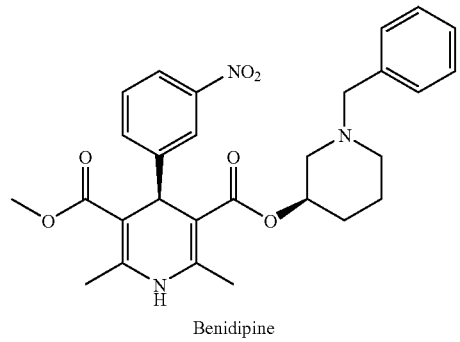
Benidipine

-continued
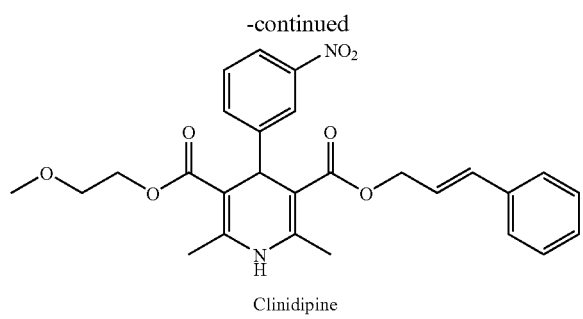
Clinidipine
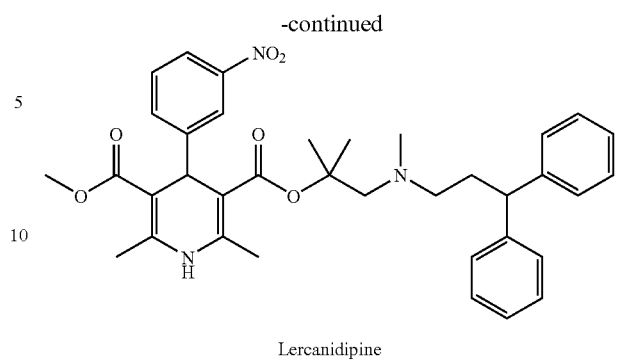
Lercanidipine
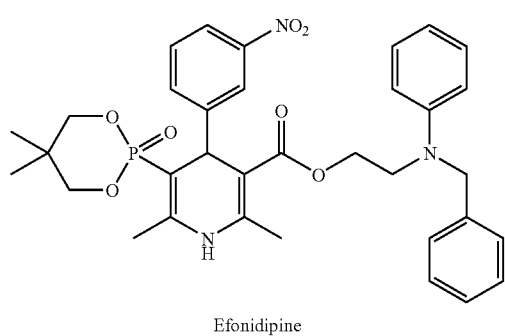
Efonidipine
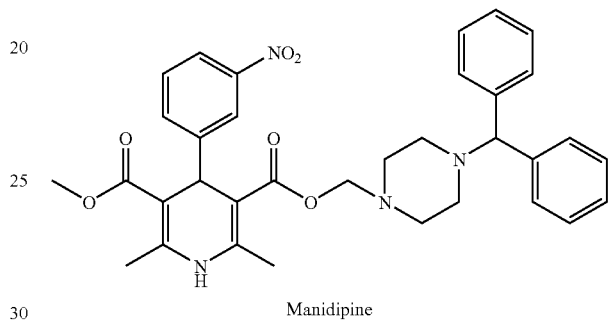
Manidipine
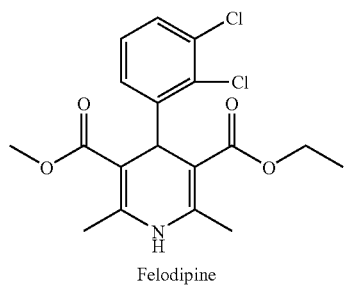
Felodipine
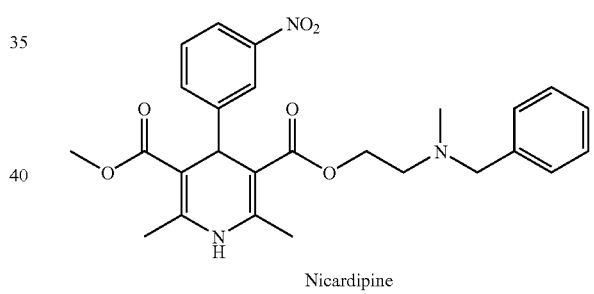
Nicardipine
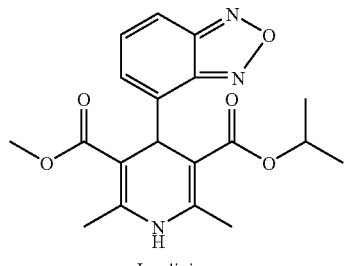
Isradipine
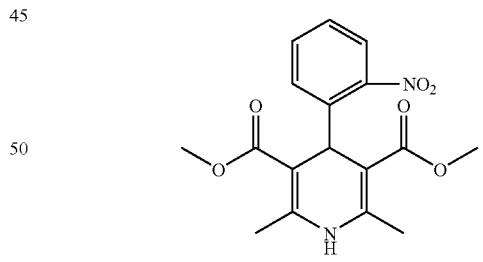
Nifedipine
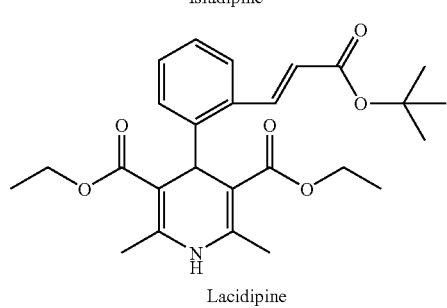
Lacidipine
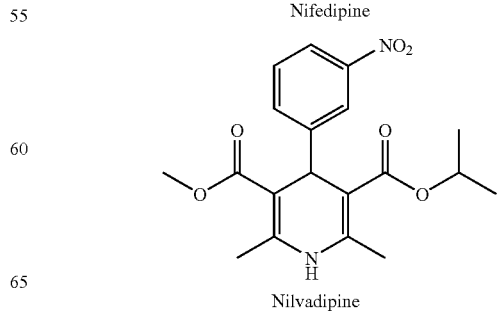
Nilvadipine -continued

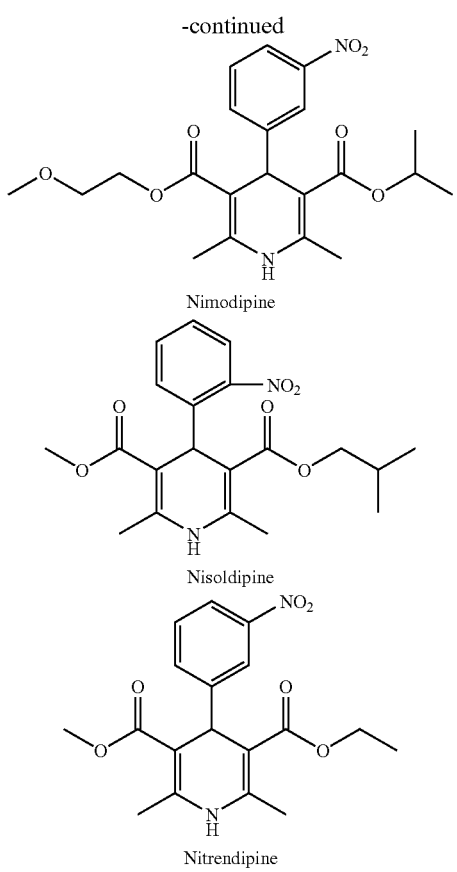

Nimodipine

Nisoldipine

Nitrendipine

None of these calcium channel blocker drugs has been shown to directly elevate α-MyHC protein levels or α-MyHC mRNA levels nor have they been shown to directly lower β-MyHC protein levels or β-MyHC mRNA levels. None of these calcium channel blocker drugs show activity in the α-MyHC and β-MyHC-based assays and tests used for determining the novel biological activity of the compounds of this invention. Raizada et al. (1993), and Raizada et al. (1999), reported that nifedipine protected against a drop in the α-MyHC/β-MyHC protein ratio in chronic hypertension and aging rats; however, the effect was not shown nor believed to be a direct effect on MyHC regulation, but rather an indirect effect of the calcium channel blocker through its antihypertensive effect. In fact, using neonatal rat ventricular myocytes it was shown by Samarel et al. (1992), and Simpson et al. (1996), that in vitro, nifedipine caused a lowering of total MyHC. Lastly, in a 12-week study by Yamazaki et al. (1998), spontaneously hypertensive rats treated with amlodipine maintained their α-MyHC/β-MyHC ratios. Therefore, these traditional calcium channel blockers have not been shown to directly affect α-MyHC/β-MyHC ratios in cardiomyocytes.

All compounds of Formula I are chiral, i.e., they are non-superimposable on their mirror image, and optically active. Some starting materials for one method of preparation of the compounds of Formula I are available from ChemBridge. These available starting materials are racemates, i.e., equal solid mixtures of the R and S enantiomers. Commercially available structures of these starting materials are represented in Formula II.

Single enantiomers different from each other in two ways. First, they rotate the plane of polarized light in equal and opposite directions. Second, and most importantly, they react independently, at different rates and in unpredictable ways with other chiral compounds, especially with complex chiral biological structures such as those of the human body. In addition to optical activity, enantiomers usually have some distinct physical properties from racemates such as melting point and solubility. However, enantiomers differ from each other only in the two ways mentioned above. Ultimately, the identity of each individual enantiomer must be proven experimentally because their physical properties and distinct interactions with chiral biological molecules and systems cannot be predicted beforehand. For reviews see March (1992); and, Burke and Henderson (2002). The separation or resolution of individual enantiomers from a racemate follows methods known by one of skill in the art.

Most frequently, only one enantiomer of a racemate usually provides a desired biological or drug effect. In fact, in many cases, the less active or inactive enantiomer of a racemic drug interacts in a distinct, unrelated and negative way providing undesirable, deleterious or toxic side effects. Therefore, single enantiomer drugs are most preferred. When researching a new mechanism-of-action-based series of compounds, it is not possible to predict which enantiomer of a racemic compound will possess the desirable drug activity. This novel and useful knowledge can only be obtained through experimentation and analysis of the experimental results. The U.S. Food and Drug Administration (FDA) offers continuing guidance for the development of optically active drugs that is available electronically and is searchable at www.fda.gov/cder/guidance/index.htm. For review see Strong (1999); and, FDA Policy Statement (1992); and, De Camp (1989); also, Note for Guidance—Investigation of Chiral Active Substances (1994).

This invention relates to the unique properties associated with the S enantiomer of the compounds of Formula I. Prior to this invention, the single enantiomer compounds of Formula I were not observed nor characterized. Prior to this invention the compounds of Formula I and II are not known to have been administered to animals, humans or other biological systems.

Certain starting materials of Formula III below, useful for the preparation of compounds of Formula I, are known in the art:

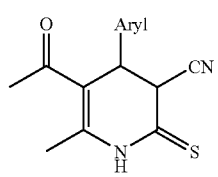

Formula III wherein aryl=phenyl, furan-2-yl and thiophen-2-yl and substitutions thereon.

Detailed preparations for these starting materials are found, for aryl=phenyl, in Krauze et al. (1984); Krauze et al. (1988); Krauze et al. (1991); Krauze et al. (1998); Krauze and Dudurs (2000); Tirzite et al. (2002); Sharanin et al. (1985); Sharanin et al. (1986); and for aryl=furan-2-yl and thiophen-2-yl in Attaby et al. (1996).

III. Methods of Treating Cardiovascular Diseases

A. Therapeutic Regimens for Hypertrophy and Heart Failure

Current medical management of cardiac hypertrophy in the setting of a cardiovascular disorder includes the use of at least two types of drugs: inhibitors of the renin-angiotensin system, and β-adrenergic blocking agents (Bristow, 1999). Therapeutic agents to treat pathologic hypertrophy in the setting of heart failure include angiotensin II converting enzyme (ACE) inhibitors and β-adrenergic receptor blocking agents (Eichhom and Bristow, 1996). Other pharmaceutical agents that have been disclosed for treatment of cardiac hypertrophy include but are not limited to angiotensin II receptor antagonists (U.S. Pat. No. 5,604,251) and neuropeptide Y antagonists (WO 98/33791). Despite currently available pharmaceutical compounds, prevention and treatment of cardiac hypertrophy, and subsequent heart failure, continues to present a major therapeutic challenge.

Non-pharmacological treatment is primarily used as an adjunct to pharmacological treatment. One means of non-pharmacological treatment involves reducing the sodium in the diet. In addition, non-pharmacological treatment also entails the elimination of certain precipitating drugs, including negative inotropic agents (e.g., certain calcium channel blockers and antiarrhythmic drugs like disopyramide), cardiotoxins (e.g., amphetamines), and plasma volume expanders (e.g., nonsteroidal anti-inflammatory agents and glucocorticoids).

In one embodiment of the present invention, methods for the treatment of cardiac hypertrophy or heart failure using compounds of Formula I are provided. For the purposes of the present application, treatment comprises reducing one or more of the symptoms of cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness (the same results may hold true for the right ventricle). In addition, use of the present invention may prevent cardiac hypertrophy and its associated symptoms from arising.

Another potential therapeutic approach is to reverse the structural changes that occur in the heart in response to hypertrophy and heart failure, a process known as cardiac remodeling. Remodeling relates specifically to the gene expression changes that occur as the heart grows more diseased. In remodeling, genes normally expressed during fetal development (fetal genes such as SERCA, α-MyHC, etc.) are expressed aberrantly (for a review see Lowes et al, 2002, hereinafter incorporated by reference). Originally these changes were thought to be irreversible, so the only hope was to provide therapy to alleviate the symptoms. However, it was eventually discovered that unloading the failing human heart by placing the patient on a left ventricular assist device could reverse some of the remodeling changes (Dipla et al., 1998). Recently it has been demonstrated that this reverse remodeling can occur through pharmaceutical therapies. (Bristow et al., 2000). Through the use of acetylcholine-esterase inhibitors, improvements in cardiac contractility have been seen and systolic function of the heart has been enhanced. (Eichorn et al., 1996; Lowes et al., 2002). Furthermore, β-adrenergic receptor blockers have been shown to upregulate mRNA levels of α-MyHC and SERCA through indirect action on other cardiac targets (Lowes et al., 2002). It is therefore plausible that treating the underlying contractile defects in the remodeled heart by directly upregulating α-MyHC would lead to a reversal of the remodeling process.

Treatment regimens would vary depending on the clinical situation. However, long term maintenance would appear to be appropriate in most circumstances.

B. Combined Therapy

In another embodiment, it is envisioned to use the present invention in combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time. Alternatively, the therapy using the claimed formulations may precede or follow administration of the other agent(s) by intervals ranging from min to weeks. In embodiments where the various agents are applied separately to the cell, one would generally ensure that a significant period of time did not expire between the time of each delivery, such that the agents would still be able to exert an advantageously combined effect on the cell. In such instances, it is contemplated that one would typically contact the cell with both modalities within about 12-24 hrs of each other and, more preferably, within about 6-12 hrs of each other, with a delay time of only about 12 hrs being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the claimed compounds, or the other agent will be desired. In this regard, various combinations may be employed. By way of illustration, where the present invention is "A" and the other agent is "B," the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated. Pharmacological therapeutic agents and methods of administration, dosages, etc., are well known to those of skill in the art (see for example, the "Physicians Desk Reference," Goodman & Gilman's "The Pharmacological Basis of Therapeutics," "Remington's Pharmaceutical Sciences," and "The Merck Index, Thirteenth Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. In addition, it should be noted that any of the following may be used to develop new sets of cardiac therapy target genes.

While it is expected that many of these genes may overlap, new gene targets likely can be developed.

a. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

i. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

ii. Resins/Bile Acid Sequesterants

Non-limiting examples of resins/bile acid sequesterants include cholestyramine (cholybar, questran), colestipol (colestid) and polidexide.

iii. HMG CoA Reductase Inhibitors

Non-limiting examples of HMG CoA reductase inhibitors include lovastatin (mevacor), pravastatin (pravochol) or simvastatin (zocor).

iv. Nicotinic Acid Derivatives

Non-limiting examples of nicotinic acid derivatives include nicotinate, acepimox, niceritrol, nicoclonate, nicomol and oxiniacic acid.

v. Thryroid Hormones and Analogs

Non-limiting examples of thyroid hormones and analogs thereof include etoroxate, thyropropic acid and thyroxine.

vi. Miscellaneous Antihyperlipoproteinemics

Non-limiting examples of miscellaneous antihyperlipoproteinemics include acifran, azacosterol, benfluorex, β-benzalbutyramide, camitine, chondroitin sulfate, clomestrone, detaxtran, dextran sulfate sodium, U.S. Pat. No. 5,8,11,14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

b. Antiarteriosclerotics

Non-limiting examples of an antiarteriosclerotic include pyridinol carbamate.

c. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

i. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

ii. Antiplatelet Agents

Non-limiting examples of antiplatelet agents include aspirin, a dextran, dipyridamole (persantin), heparin, sulfinpyranone (anturane) and ticlopidine (ticlid).

iii. Thrombolytic Agents

Non-limiting examples of thrombolytic agents include tissue plasminogen activator (activase), plasmin, pro-urokinase, urokinase (abbokinase) streptokinase (streptase), anistreplase/APSAC (eminase).

d. Blood Coagulants

In certain embodiments wherein a patient is suffering from a hemhorrage or an increased likelyhood of hemhorraging, an agent that may enhance blood coagulation may be used. Non-limiting examples of a blood coagulation promoting agent include thrombolytic agent antagonists and anticoagulant antagonists.

i. Anticoagulant Antagonists

Non-limiting examples of anticoagulant antagonists include protamine and vitamine K1.

ii. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

e. Antiarrhythmic Agents

Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents.

i. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocainide (tonocard) and mexiletine (mexitil). Non-limiting examples of Class IC antiarrhythmic agents include encainide (enkaid) and flecainide (tambocor).

ii. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

iii. Repolarization Prolonging Agents

Non-limiting examples of an agent that prolong repolarization, also known as a Class III antiarrhythmic agent, include amiodarone (cordarone) and sotalol (betapace).

iv. Calcium Channel Blockers/Antagonist

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (amlodipine) calcium antagonist.

v. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

f. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

i. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

ii. Alpha/Beta Blockers

In certain embodiments, an antihypertensive agent is both an alpha and beta adrenergic antagonist. Non-limiting examples of an alpha/beta blocker comprise labetalol (normodyne, trandate).

iii. Anti-Angiotension II Agents

Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-IL type-1 receptor blocker (ARBS), include angiocandesartan, eprosartan, irbesartan, losartan and valsartan.

iv. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet).

Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

v. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

vi. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

h. Treatment Agents for Congestive Heart Failure

Non-limiting examples of agents for the treatment of congestive heart failure include anti-angiotension II agents, afterload-preload reduction treatment, diuretics and inotropic agents.

i. Afterload-Preload Reduction

In certain embodiments, an animal patient that can not tolerate an angiotension antagonist may be treated with a combination therapy. Such therapy may combine adminstration of hydralazine (apresoline) and isosorbide dinitrate (isordil, sorbitrate).

ii. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

iii. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

i. Antianginal Agents

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

c. Pharmaceutical Formulations

It will be understood that in the discussion of formulations and methods of treatment, references to the compounds of Formula I and Formula II are meant to also include the pharmaceutically acceptable salts, as well as pharmaceutical compositions comprising these compounds. Also provided are treatments of cardiovascular disease, comprising administering to a subject an effective amount of a compound of Formula I, its pharmaceutically acceptable salts, and a pharmaceutically acceptable carrier or formulation.

In specific embodiments of the invention the pharmaceutical formulation will be formulated for delivery via rapid release, other embodiments contemplated include but are not limited to timed release, delayed release, and sustained release. The formulation can be an oral suspension in either the solid or liquid form. In further embodiments, it is contemplated that the formulation can be prepared for delivery via parenteral delivery, or used as a suppository, or be formulated for subcutaneous, intravenous, intramuscular, intraperitoneal, sublingual, transdermal, or nasopharyngeal delivery.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release (hereinafter incorporated by reference).

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ordinary temperatures, but liquid at the rectal temperature and will therefore melt in the rectum to release the drug. Such materials are cocoa butter and polyethylene glycols.

For topical use, creams, ointments, jellies, gels, epidermal solutions or suspensions, etc., containing the compound of Formula I are employed. For purposes of this application, topical application shall include mouthwashes and gargles.

The formulation may also be administered as nanoparticles, liposomes, granules, inhalants, nasal solutions, or intravenous admixtures.

The previously mentioned formulations are all contemplated for treating patients suffering from cardiovascular disease. Cardiovascular disease includes but is not limited to pathological hypertrophy, chronic and acute heart failure.

The amount of active ingredient in any formulation may vary to produce a dosage form that will depend on the particular treatment and mode of administration. It is further understood that specific dosing for a patient will depend upon a variety of factors including age, body weight, general health, sex, diet, time of administration, route of administration, rate of excretion, drug combination and the severity of the particular disease undergoing therapy.

IV. Methods of Preparation and Synthesis

The compounds of the present invention can be prepared according to the following methods.

A. Method A

In many cases the compounds of Formula I can be prepared from the appropriate racemate of Formula II by preparative chromatographic separation using a chiral solid phase. High-performance liquid chromatography (HPLC) is the most common technique used for such a separation. High pressure, medium pressure, low pressure and atmosphere pressure liquid chromatography can be used for such a separation. Many liquid phases and chiral solid phases are available for this type of application: for a review see Francotte (2001); and Anderson and Allenmark (2002). For a review of semipreparative applications see Inotsume and Nakano (2002); and Boatto et al. (2003). Related examples are found in Dolle et al. (1997); and Alajarin et al. (1995).

In other embodiments of Method A the racemate to be separated may first be derivatized with an achiral or chiral derivatizing agent to enhance the resolution and separation efficiency; the solid phase may be prepared as an imprinted polymer from one or the other of the enantiomers to be separated; in some cases separations may be achieved using an achiral solid phase with chiral additives in the liquid phase; in some cases separations may be achieved using an achiral solid phase and a racemate derivatized with a chiral reagent; for a review see Toyo'oka (2002).

B. Method B

The general scheme of Method B follows that in Krauze et al. (1984); Krauze et al. (1988); Krauze and Dudurs (2000); Krauze et al. (1998); Sharanin et al. (1985); Sharanin et al. (1986); Tirzite et al. (2002), and Attaby et al. (1996). The starting material aldehydes and 1,3-diketones are available commercially or from extensive processes for their or related compound preparation in the literature and readily adaptable by one skilled in the art. 2-Cyanothioacetamide is commercially available. Ethanol is a suitable solvent and piperidine and morpholine are suitable bases to catalyze the ring formation in step 1. Step 1 is typically conducted at room temperature but may be performed at lower or moderately higher temperatures. Step 2 is a hydrolysis of the intermediate salt of A. If desired A may be isolated and purified by crystallization or chromatography. Ethanol is a suitable solvent and piperidine and morpholine are suitable bases to catalyze the alkylation in step 3. Leaving groups on the alkylating agent other than bromine, e.g., iodine and triflate, may also be useful in step 3. Step 3 is typically conducted at room temperature but may be performed at lower or moderately higher temperatures. Steps 1 and 3 may be combined without step 2 or isolation of any intermediate. If necessary, purification can be achieved by one skilled in the art with standard procedures.

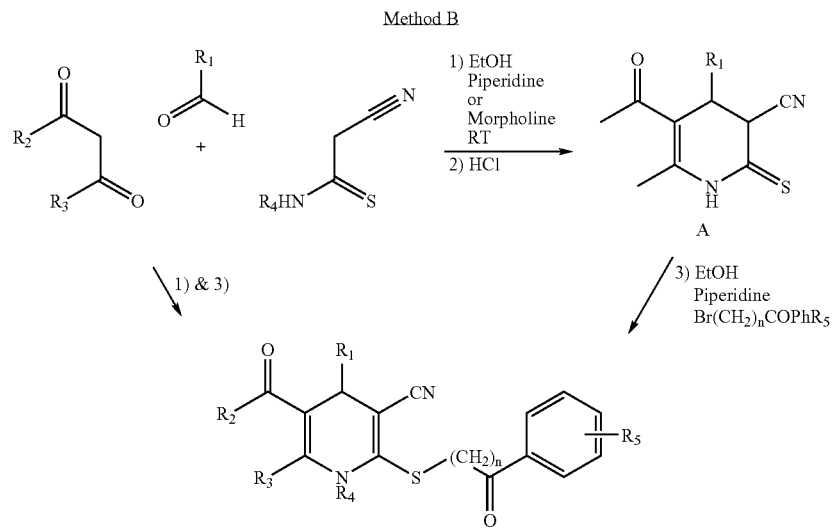

with R-groups as in Formula II.

C. Method C

The racemate to be separated is first reacted with a chiral derivatizing agent to yield a mixture of diastereomers. These diastereomers may then be separated by one skilled in the art using standard techniques such as crystallization or chromatography. Following separation and isolation of the individual diastereomers the chiral derivatizing group previously added is removed using methods known by one skilled in the art and the individual pure enantiomers are obtained, further purified if necessary, and characterized. March (1992).

D. Method D

The racemate to be separated is first reacted with a chiral agent that forms a diastereomeric salt mixture from the racemate. For example chiral acids and chiral amines. The diastereomeric salts are then separated by one skilled in the art and frequently utilizing crystallization techniques. The separated diastereomeric salts are then freed of the chiral salt forming agent by one skilled in the art to yield the individual enantiomers, which can be further purified if necessary, and characterized. March (1992).

E. Method E

The desired enantiomer may be prepared by one skilled in the art through the application of chiral or asymmetric synthesis. In this method a chiral and optically active staring material or building block added during the synthesis dictates the enantiomer synthesized.

In another embodiment of Method E a chiral reagent, not incorporated into the final compound, is used during the synthesis to direct selective formation of chirality in the compound with formation of a single enantiomer. Related examples are Iqbal et al. (1994); Meyers and Oppenlaender (1986); and Enders et al. (1988). For more review see Iida and Mase (2002), and Hillier and Reider (2002).

In another embodiment of Method E one skilled in the art may apply bioprocesses to the asymmetric synthesis of the desired enantiomers; for a review see Patel (2001), and Huisman and Gray (2002).

In another embodiment of Method E one skilled in the art may use deracemization at some point during a synthesis of the desired enantiomers. Deracemization processes may be afforded by either bioprocess or non-bioprocess techniques. March (1992)

In another embodiment of Method E one skilled in the art may be able to use kinetic resolution to achieve an asymmetric synthesis or separation of the desired enantiomers. March (1992).

F. Method F

In certain cases one skilled in the art may be able to use chiral recognition of individual enantiomers by a chiral ligand to afford a feasible separation of enantiomers in a racemate. March (1992).

V. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation and culture of neonatal rat ventricular myocytes (NRVM) was performed by removing hearts from 1-3 day old rat neonatal pups, along with the atria and lungs. The ventricles were cut into smaller pieces and digested 3 times with collagenase for 20-30 min at 37° C. The myocytes were then separated from other cell types using a Percoll gradient. The myocyte layer was collected, washed 2 times, and plated on tissue culture grade 10 cm Petri dishes for 1-2 hrs. The non-adherent cells (myocytes) were removed and plated in Costar clear view 96 well plates coated with 0.2% gelatin for at least 2 hrs. The gelatin solution was removed, and the myocytes were resuspended in DMEM high glucose media (Mediatech) containing 10% charcoal/dextran treated FBS (Hyclone) and 1% Penicillin-Streptomycin-Glutamine (PSG, Gibco). Ten thousand NRVM were plated per well in a 100 μl volume, and incubated overnight at 37° C. in 5% $CO_2$ in air. The following day, the media was replaced with 100 μl of serum-free DMEM high glucose medium supplemented with PSG and 0.3% Nutridoma-SP (Roche).

Compounds were reconstituted in DMSO at 30 mM, and aliquots were stored at −20° C. A 1:1000 dilution was prepared in serum-free DMEM medium supplemented with PSG and 0.3% Nutridoma, and sonicated for 5 min at room temperature. After sonication, additional 3 fold dilutions were prepared in the same medium. Diluted compound was then added to the NRVM cultures in a volume of 100 μl. A 100 mM thyroid hormone stock solution (T3, Calbiochem) was prepared in 100 mM NaOH and added at a final concentration of 3 nM in DMEM medium supplemented with PSG and 0.3% Nutridoma-SP (Roche). NRVM were cultured for 3 days before detection of α-myosin heavy chain (α-MyHC) protein levels in the cytoblot assay.

For the α-MyHC cytoblot assay, NRVM cultures were analyzed for α-MyHC protein levels after 3 days of incubation. NRVM were washed 2 times with PBS, fixed with methanol for 30 min at 4° C., and washed an additional 2 times with PBS. Blocking solution consisting of PBS with 1% bovine serum albumin (BSA, Fisher Biotech) was added for 1 hr at room temperature before addition of a saturating amount of supernatant containing an α-MyHC specific antibody for 60 min at room temperature (BA-G5 hybridoma, ATTC). Two washes were performed with PBS/1% BSA, and a 1:500 dilution of HRP-goat anti-mouse IgG (Southern Biotech) diluted in PBS/1% BSA was added for 60 min at room temperature. Excess antibody was removed with 3 PBS washes, and a chemiluminescent substrate was added (Pierce SuperSignal West Pico Chemiluminscent Substrate) for 5 min before quantitation on a Packard Fusion Plate Reader.

The following compounds, available commercially from ChemBridge Corporation (San Diego, Calif.), showed measurable activity in the α-MyHC and β-MyHC-based assays and tests used for determining the novel biological activity of the compounds of this invention.

TABLE 1

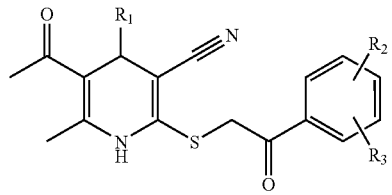

| Compound Number | R1 | R2 | R3 | % increase of a-MyHC over baseline at 10 mM Cpd |
|---|---|---|---|---|
| 1 | 2-Cl-Phenyl | 3-$NO_2$ | H | 206 |
| 2 | 3-$CH_3$-Phenyl | 3-$NO_2$ | H | 95 |
| 3 | 2-Cl-Phenyl | 2-Cl | 5-Cl | 314 |
| 4 | 2-Cl-Phenyl | 2-Cl | H | 135 |
| 5 | 2-Cl-Phenyl | 4-Cl | H | 52 |
| 6 | 2-Cl-Phenyl | 4-Br | H | 53 |
| 7 | 4-Cl-Phenyl | 3-Cl | 4-Cl | 43 |
| 8 | 4-Cl-Phenyl | 2-Cl | 4-Cl | 29 |
| 9 | 4-Cl-Phenyl | 2-Cl | H | 80 |
| 10 | 4-F-Phenyl | 3-Cl | 4-Cl | 88 |
| 11 | 4-F-Phenyl | 2-Cl | 4-Cl | 51 |
| 12 | 3-$NO_2$-Phenyl | 4-Br | H | 34 |
| 13 | Phenyl | 3-Cl | 4-Cl | 95 |
| 14 | 2-Cl-Phenyl | 4-$NO_2$ | H | 24 |
| 15 | Phenyl | 2-Cl | 4-Cl | 81 |
| 16 | Phenyl | 3-Br | H | 143 |
| 17 | Phenyl | 4-Cl | H | 29 |
| 18 | Phenyl | 4-F | H | 37 |
| 19 | Phenyl | H | H | 71 |
| 20 | 3-$CH_3$-Phenyl | 3-Cl | 4-Cl | 79 |
| 21 | 2-Cl-Phenyl | 3-Cl | 4-Cl | 126 |
| 22 | 2-Cl-Phenyl | 2-Cl | 4-Cl | 81 |
| 23 | 4-Br-Phenyl | 2-Cl | 5-Cl | 70 |
| 24 | 4-$C_2H_5$-Phenyl | 3-$NO_2$ | H | 130 |
| 25 | 4-Cl-Phenyl | 3-$NO_2$ | H | 139 |
| 26 | 2-Cl-Phenyl | H | H | 161 |
| 27 | Phenyl | 2-Cl | 5-Cl | 303 |
| 28 | Phenyl | 4-$NO_2$ | H | 125 |
| 29 | 3-$NO_2$-Phenyl | 3-Cl | 4-Cl | 201 |
| 30 | Thiophen-2-yl | 3-$NO_2$ | H | 156 |
| 31 | Thiophen-2-yl | 3-Cl | 4-Cl | 151 |
| 32 | Thiophen-2-yl | 2-Cl | 4-Cl | 45 |
| 33 | Thiophen-2-yl | 2-Cl | 5-Cl | 181 |
| 34 | Furan-2-yl | 2-Cl | 4-Cl | 97 |
| 35 | Furan-2-yl | 3-Cl | 4-Cl | 125 (at 3 mM) |
| 36 | Furan-2-yl | 4-$NO_2$ | H | 115 |

As shown above in Table 1, Compound 1 increased α-MyHC protein levels as determined by an α-MyHC cytoblot assay. Compound 1 was added to NRVM at concentrations ranging from 3 nM to 30 μM. After 3 days of incubation with NRVM, α-MyHC protein levels were detected in the cytoblot assay and quantitated (FIG. 1). Increasing amounts of Compound 1 resulted in progressively higher levels of α-MyHC protein levels relative to unstimulated NRVM (no compound added, set to 100%). An increase in α-MyHC protein levels was first detected beginning at 30 nM, with a maximal response observed at 3 μM. In six independent experiments, the concentration of Compound 1 that gave a half-maximal response was on average 60 nM.

Example 2

Compounds of Formula IV below are available commercially from ChemBridge Corporation (San Diego, Calif.). None of the compounds of Formula IV show activity in the α-MyHC and β-MyHC-based assays and tests used for determining the novel biological activity of the compounds of this invention.

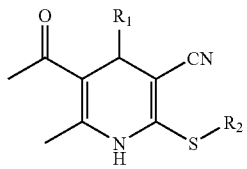

Formula IV wherein $R_1$=phenyl, and $R_2$=methyl;
$R_1$=2-chlorophenyl, and $R_2$=methyl, ethyl and $CH_2CONHPhenyl$;
$R_1$=4-chlorophenyl, and $R_2$=methyl, ethyl and 3-nitrobenzyl;
$R_1$=4-bromophenyl, and $R_2$=3-nitrobenzyl;
$R_1$=4-ethylphenyl, and $R_2$=$CH_2CONH_2$ and 3-methylbut-2-enyl;
$R_1$=2-nitropheny,l and $R_2$=butyl;
$R_1$=3-nitrophenyl, and $R_2$=benzyl;
$R_1$=4-hydroxyphenyl, and $R_2$=$CH_2CONH_2$;
$R_1$=furan-2-yl, and $R_2$=butyl and 3-methylbut-2-enyl;
$R_1$=furan-3-yl, and $R_2$=3-nitrobenzyl;
$R_1$=thiophen-2-yl, and $R_2$=butyl, 3-methylbut-2-enyl and benzyl; and,
$R_1$=3-methylthiophen-2-yl, and $R_2$=butyl and benzyl Example 3

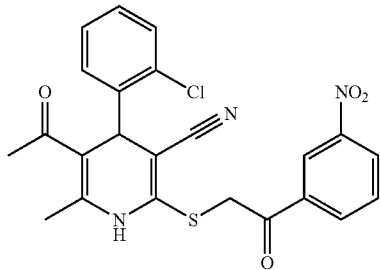

Compound 1

Figure 2:
FIG. 2 Effect of Compound 1 on α-MyHC protein levels as detected by Western blotting. NRVM are stimulated with Compound 1 at different concentrations for 3 days. Protein extracts are prepared, proteins are separated by SDS-PAGE electrophoresis, transferred to PVDF membrane, and detected with an anti-α-MyHC monoclonal antibody.

As an independent measure of changes in α-MyHC protein levels, NRVM stimulated with Compound 1 were analyzed for α-MyHC protein levels by Western blotting. Protein extracts prepared from NRVM stimulated with a range of concentrations of Compound 1 from 10 nM to 10 μM were separated by SDS-PAGE and transferred to PVDF membrane. Levels of α-MyHC protein were detected by Western blotting using the same anti-α-MyHC monoclonal antibody used in the cytoblot assay. As shown in FIG. 2, increasing amounts of α-MyHC protein were observed with increasing amounts of Compound 1. This experiment verified that the changes in α-MyHC protein detected in the cytoblot assay were also evident by Western blotting. In addition, the increase in α-MyHC protein levels observed with T3 was similar to the increase seen with higher concentrations of Compound 1.

Example 4

Anti-hypertrophic Activity of Racemic Compound 1 and the Purified Enantiomers of Compound 1. Neonatal rat ventricular myocytes (NRVM) were isolated from 1 to 3 day-old Sprague-Dawley rats using enzymatic digestion and myocyte enrichment techniques. NRVM were cultured in serum-containing media for 18 hours. For the continuation of culture, serum-free media was used. Hypertrophy of NRVM was induced using pharmacological stimuli, including phenylephrine, endothelin-1, and angiotensin I. Hypertrophic responses were determined using methods including the following: measurement of total cellular protein; secretion of atrial natriuretic factor; determination of cell volume; determination of the expression of so-called fetal genes such as atrial natriuretic factor, beta-myosin heavy chain and alpha-skeletal actin. ANF secretion was the most sensitive assay for measuring hypertrophy, and the $IC_{50}$ of the ANF ELISA was the measurement used to determine antihypertrophic activity. The $IC_{50}$ for the racemate was measured as 0.427 μM, the S-enantiomer was 0.389 μM and the R-enantiomer was 1.101 μM.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 5,604,251.
U.S. Pat. No. 4,265,874.

U.S. Pat. No. 4,256,108.
U.S. Pat. No. 4,166,452.
Abraham et al., *Mol Med.*, 8(11):750-60, 2002.
Alajarin et al., *J Medicinal Chem.*, 38:2830, 1995.
Anderson and Allenmark, *J. Biochem. Biophysical Methods*, 54:11, 2002.
Arai et al., *Circ. Res.*, 72:463, 1993.
Attaby et al., *Phosphorous, Sulfur and Silicone and Related Elements*, 119:1, 1996.
Boatto et al., *Chirality*, 15:494, 2003.
Bouvagnet et al., *Basic Res. Cardiol.*, 84:91-102, 1989.
Bristow, *Circulation*, 101(5):558-569, 2000.
Bristow, *Cardiology*, 92:3-6, 1999.
Burke and Henderson, *Brit. J. Anaesthesia*, 88:563, 2002.
De Camp, *Chirality*, 1:2, 1989.
Dipla et al., *Circulation*, 97(23):2316-2322, 1998.
Dolle et al., *Bioorganic Med. Chem.*, 5:749, 1997.
Durand et al., *Ann. Med.*, 27:311-317, 1995.
Eichhorn and Bristow, *Circulation*, 94:2285-2296, 1996.
Enders et al., *Tetrahedron Letters*, 29:6437, 1988.
FDA Policy Statement, *Chirality*, 4:338, 1992.
Francotte, *J. Chromatography A*, 906:379, 2001.
Goodman & Gilman's *The Pharmacological Basis Of Therapeutics*, Hardman et al. ed., 10th ed., 32:853-860; 35:891-893, 2001.
Hajjar et al., *Circulation*, 86(6):1819-1826, 1992.
Hillier and Reider, *Drug Discovery Today*, 7:303. 2002.
Huisman and Gray, *Current Opinion in Biotechnology*, 13:352, 2002.
Iida and Mase, *Current Opinion in Drug Discovery and Development*, 5:834, 2002.
Inotsume and Nakano, *J. Biochem. Biophysical Methods*, 54:255, 2002.
Iqbal et al., *Chirality*, 6:515, 1994.
Krauze and Dudurs, *Chemistry of Heterocyclic Compounds*, 36:693, 2000.
Krauze et al., *Khimiko-Farmatsevticheskii Zhurnal*, 25:40, 1991.
Krauze et al., *Khimiko-Farmatsevticheskii Zhurnal*, 22:548, 955, 1988.
Krauze et al., *Khimiya Geterotsiklicheskikh Soedinenii*, 1694, 1984.
Krauze et al., *Tetrahedron*, 54:9161, 1998.
Lowes et al., *J. Invest. Med.*, 43:316A, 1995.
Lowes et al., *J. Clin. Invest.*, 100(9):2315-2324, 1997.
Lowes et al., *N. Engl. J. Med.*, 346(18):1346-13467, 2002.
March, *Advanced Organic Chemistry*, 4th ed., Chapter 4, page 94, 1992.
Marian and Roberts, *Circulation*, 92:1336-1347, 1995.
Meyers and Oppenlaender, *J. Chem. Soc. Chem. Communications*, 920, 1986.
Miyata et al., *Circ. Res.*, 86(4):386-390, 2000.
Nakao et al., *J. Clin. Invest.*, 100(9):2362-2370, 1997.
Niimura et al., *Circulation*, 105(4):446-451, 2002.
Note for Guidance—Investigation of Chiral Active Substances. Brussels: *Commission of the European Union*, 111/3601/91, 1994.
Pagani et al., *Circ. Res.*, 63(2):380-385, 1988.
Patel, *Current Opinion in Biotech.*, 12:587, 2001.
PCT Patent Application No. WO 98/33791
Raizada et al., *Molecular and Cell Biochemistry*, 198:109, 1999.
Raizada et al., *Cardiovascular Res.*, 27:1869, 1993.
Reiser et al., *Am. J. Physiol. Heart. Circ. Physiol.*, 280(4):H1814-H1820, 2001.
Remington's Pharmaceutical Sciences, 15th ed., 1035-1038, 1570-1580, Mack Publishing Co., PA, 1980.
Samarel et al., *American J. Physiology*, 263:C642, 1992.
Schwartz et al., *Circulation*, 91:532-540, 1995.
Sharanin et al., *Zhurnal Organicheskoi Khimii*, 22:2600, 1986.
Sharanin et al., *Zhurnal Organicheskoi Khimii*, 21:683, 1985.
Simpson et al., *American J. Physiology*, 270:C1075, 1996.
Strong, *Food and Drug Law Journal*, 54:463, 1999.
The Merck Index, O'Neil et al., ed., 13th ed., 2001.
Thierfelder et al., *Cell*, 77:701-712, 1994.
Tirzite et al., *Chem. Heterocyclic Compounds*, 38:795, 2002.
Toyo'oka, *J. Biochemical and Biophysical Methods*, 54:25, 2002.
Watkins et al., *N. Enql. J. Med.*, 326:1108-1114, 1992.
Yamazaki et al., *Hypertension*, 31:32, 1998.
Young et al., *Handbook of Applied Therapeutics*, 7.1-7.12 and 9.1-9.10, 1989.

What is claimed is:

1. A composition comprising a carrier or excipient and an optically active compound having the Formula I:

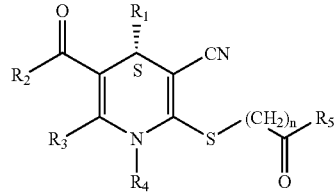

Formula I or a and pharmaceutically acceptable salt thereof, wherein:
$R_1$ and $R_5$ are, independently, phenyl, pyridine, pyrimidine, thiophene, furan, oxazole, isoxazole, thiazole, isothiazole, imidazole and pyrazole, and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2$NH—$C_{0-4}$-alkyl, $SO_2$N($C_{1-4}$-alkyl$)_2$, $NHSO_2$—$C_{1-4}$-alkyl, CONH—$C_{0-4}$-alkyl, NHCO—$C_{1-4}$-alkyl and COO—$C_{0-4}$-alkyl;
wherein $R_2$ is $C_{1-4}$-alkyl; $R_3$ and $R_4$ are $C_{0-4}$-alkyl; and alkyl may be straight or branched chain; and
wherein n is 1-4;
wherein the composition is substantially free of the R-form.

2. The composition of claim 1, wherein the S enantiomer of said compound is greater than 70% pure, greater than 75% pure, greater than 80% pure, greater than 85% pure, greater than 90% pure, greater than 95% pure, greater than 96% pure, greater than 97% pure, greater than 98% pure, or greater than 99% pure.

3. The composition of claim 1, wherein $R_1$ and $R_5$ are, independently, phenyl, thiophene, furan, oxazole and thiazole; and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2$NH—$C_{0-4}$-alkyl, $SO_2$N($C_{1-4}$-alkyl$)_2$, $NHSO_2$—$C_{1-4}$-alkyl, CONH—$C_{0-4}$-alkyl, NHCO—$C_{1-4}$-alkyl and COO—$C_{0-4}$-alkyl.

4. The composition of claim 3, wherein $R_1$ and $R_5$ are, independently, phenyl, thiophene and furan; and any of $R_1$ and $R_5$ may be optionally substituted by one or more of halogen, $NO_2$, CN, $CF_3$, $C_{1-4}$-alkyl, $C_{0-4}$-alkyl-O, $(C_{1-4}$-alkyl$)_2$—N, $SO_2$NH—$C_{0-4}$-alkyl, $NHSO_2$—$C_{1-4}$-alkyl, CONH—$C_{0-4}$-alkyl, NHCO—$C_{1-4}$-alkyl and COO—$C_{0-4}$-alkyl; and $R_3$ is $C_{1-4}$-alkyl.

5. The composition of claim 4, wherein:
$R_2$ is $CH_3$;
$R_3$ is $CH_3$;
$R_4$ is $C_{0-1}$-alkyl; and
n is 1-2.

6. The composition of claim 5, wherein $R_1$ and $R_5$ are, independently phenyl; and any of $R_1$ and $R_5$ may be substituted by one or more of Br, Cl, F, $NO_2$, $CF_3$, $CH_3$, $CH_3O$, $(C_{1-4}$-alkyl$)_2$—N, CONH—$C_{0-4}$-alkyl, NHCO—$C_{1-4}$-alkyl and COO—$C_{0-4}$-alkyl; and $R_4$ is H.

7. The composition of claim 6, wherein n is 1.

8. The composition of claim 7 wherein $R_1$ and $R_5$ are, independently, phenyl; and any of $R_1$ and $R_5$ may be substituted by one or more of Cl, F, $NO_2$, $CF_3$, $CH_3$, $CH_3O$.

9. A pharmaceutical formulation comprising comprising a pharmaceutically acceptable carrier and comprising an optically active compound having the Formula I:

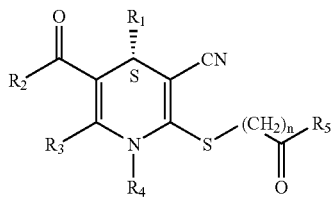

Formula I or a pharmaceutically acceptable salt thereof, wherein:
$R_1$ and $R_5$ are, independently, phenyl, pyridine, pyrimidine, thiophene, furan, oxazole, isoxazole, thiazole, isothiazole, imidazole and pyrazole, and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2$NH—$C_{0-4}$-alkyl, $SO_2$N($C_{1-4}$-alkyl$)_2$, $NHSO_2$—$C_{1-4}$-alkyl, CONH—$C_{0-4}$-alkyl, NHCO—$C_{1-4}$-alkyl and COO—$C_{0-4}$-alkyl;
wherein $R_2$ is $C_{1-4}$-alkyl; $R_3$ and $R_4$ are $C_{0-4}$-alkyl; and alkyl may be straight or branched chain; and
wherein n is 1-4;
wherein the pharmaceutical formulation is substantially free of the R-form.

10. A method for treating cardiovascular disease in a patient comprising administering to said patient pharmaceutical formulation comprising a pharmaceutically acceptable carrier and comprising an optically active compound having the Formula I:

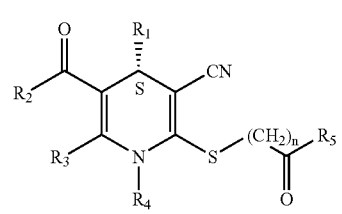

Formula I or a pharmaceutically acceptable salt thereof, wherein:
$R_1$ and $R_5$ are, independently, phenyl, pyridine, pyrimidine, thiophene, furan, oxazole, isoxazole, thiazole, isothiazole, imidazole and pyrazole, and any of $R_1$ and $R_5$ may be optionally substituted by one or more of halogen, $NO_2$, CN, $CF_3$, $C_{1-4}$-alkyl, $C_{0-4}$-alkyl-S, $C_{0-4}$-alkyl-O, $C_{0-4}$-alkyl-NH, $(C_{1-4}$-alkyl$)_2$—N, $C_{1-4}$-alkyl-SO, $C_{1-4}$-alkyl-$SO_2$, $SO_2$NH—$C_{0-4}$-alkyl, $SO_2$N($C_{1-4}$-alkyl$)_2$, $NHSO_2$—$C_{1-4}$-alkyl, CONH—$C_{0-4}$-alkyl, NHCO—$C_{1-4}$-alkyl and COO—$C_{0-4}$-alkyl;
wherein $R_2$ is $C_{1-4}$-alkyl; $R_3$ and $R_4$ are $C_{0-4}$-alkyl; and alkyl may be straight or branched chain; and
wherein n is 1-4;
wherein the pharmaceutical formulation is substantially free of the R-form.

11. The method of claim 10, wherein cardiovascular disease includes pathological hypertrophy, chronic heart failure, or acute heart failure.

12. The method of claim 10, further comprising providing an additional pharmaceutical composition to said patient.

13. The method of claim 12, wherein said additional pharmaceutical composition is selected from the group consisting of "beta blockers," anti-hypertensives, cardiotonics, anti-thrombotics, vasodilators, hormone antagonists, endothelin antagonists, cytokine inhibitors/blockers, calcium channel blockers, phosphodiesterase inhibitors and angiotensin type 2 antagonists.

* * * * *

UNITED STATES PATENT AND TRADEMARK OFFICE
CERTIFICATE OF CORRECTION

PATENT NO. : 7,485,653 B2 Page 1 of 1
APPLICATION NO. : 10/980605
DATED : February 3, 2009
INVENTOR(S) : Kathy Schreiber et al.

It is certified that error appears in the above-identified patent and that said Letters Patent is hereby corrected as shown below:

In cover page, item (75) Inventors, line 1, delete "Westminister" and insert --Westminster-- therefor.

In claim 1, column 30, line 32, delete "and".

In claim 9, column 31, line 16, delete "comprising comprising" and insert --comprising-- therefor.

Signed and Sealed this

Seventh Day of April, 2009

JOHN DOLL
*Acting Director of the United States Patent and Trademark Office*